United States Patent
Halkyard

(10) Patent No.: US 7,325,675 B2
(45) Date of Patent: Feb. 5, 2008

(54) ADHESIVELY-SECURABLE MIRROR WIPE ASSEMBLY

(76) Inventor: Douglas R. Halkyard, 4300 Sandridge Rd., Morris, IL (US) 60450

( * ) Notice: Subject to any disclaimer, the term of this patent is extended or adjusted under 35 U.S.C. 154(b) by 407 days.

(21) Appl. No.: 10/957,889

(22) Filed: Oct. 4, 2004

(65) Prior Publication Data

US 2005/0115856 A1    Jun. 2, 2005

Related U.S. Application Data

(63) Continuation-in-part of application No. 10/213,820, filed on Aug. 8, 2002, now abandoned.

(51) Int. Cl.
*B65D 81/24* (2006.01)
*B65D 83/08* (2006.01)
*B08B 1/00* (2006.01)

(52) U.S. Cl. .............. 206/207; 206/210; 206/361; 206/813; 15/104.93

(58) Field of Classification Search ........... 206/205, 206/207–210, 361–362, 484, 494, 815, 820, 206/813; 15/104.93, 104.94
See application file for complete search history.

(56) References Cited

U.S. PATENT DOCUMENTS

| | | | | |
|---|---|---|---|---|
| 2,120,204 A | * | 6/1938 | Langhorst | 206/820 |
| 2,983,369 A | * | 5/1961 | Rogovin | 206/209 |
| 3,005,543 A | * | 10/1961 | Morse | 206/205 |
| 3,563,371 A | * | 2/1971 | Heinz | 206/361 |
| 3,619,280 A | * | 11/1971 | Scheuer | 15/104.93 |
| 3,635,567 A | * | 1/1972 | Richardson, Jr. | 206/210 |
| 3,954,642 A | * | 5/1976 | Schwuger | 15/104.93 |
| 4,998,984 A | * | 3/1991 | McClendon | 206/205 |
| 5,046,608 A | * | 9/1991 | Laipply | 206/209 |
| 5,368,581 A | * | 11/1994 | Smith et al. | 206/210 |
| 5,738,212 A | * | 4/1998 | Pollard et al. | 206/210 |
| 6,762,157 B1 | * | 7/2004 | Babinski et al. | 510/101 |
| 2002/0174500 A1 | * | 11/2002 | Micciche et al. | 15/104.93 |

* cited by examiner

*Primary Examiner*—Bryon P. Gehman
(74) *Attorney, Agent, or Firm*—Cherskov & Flaynik

(57) ABSTRACT

A mirror wipe assembly for use in particular by dentists consists of an absorbent strip of material on a backing strip saturated with a defogging substance for transfer to the surface of the mirror used by such dentist to look within the mouth of a patient, by wiping the saturated absorbent strip across the mirror's surface. A single absorbent strip with its backing strip are enclosed within the impervious sealed pocket of a metalized flexible sheet pouch that is impervious to penetration by liquid or gaseous materials. The pouch may be opened for entrance to the pouch by pulling apart or by cutting. The pouch includes an adhesive strip with a peel off cover strip on the back of the pouch for the dentist or other user to adhere the pouch to a convenient location while working on a patient.

18 Claims, 4 Drawing Sheets

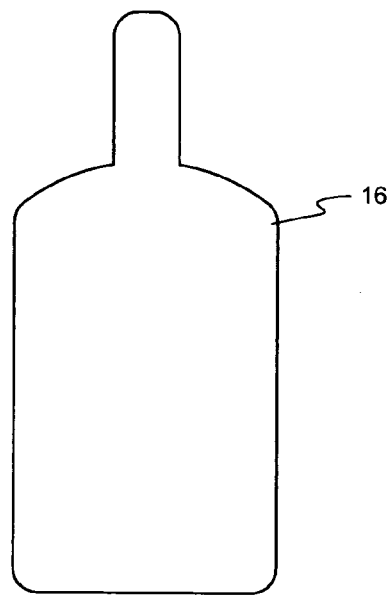
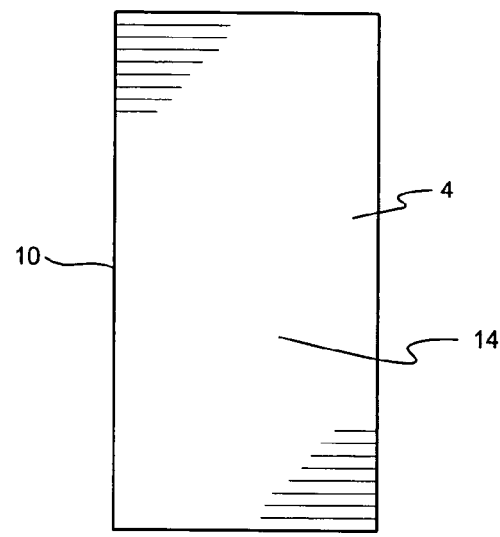
Fig. 4
Fig. 5
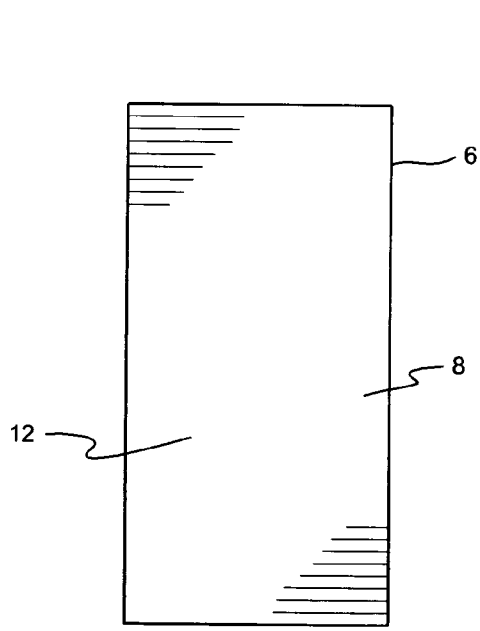
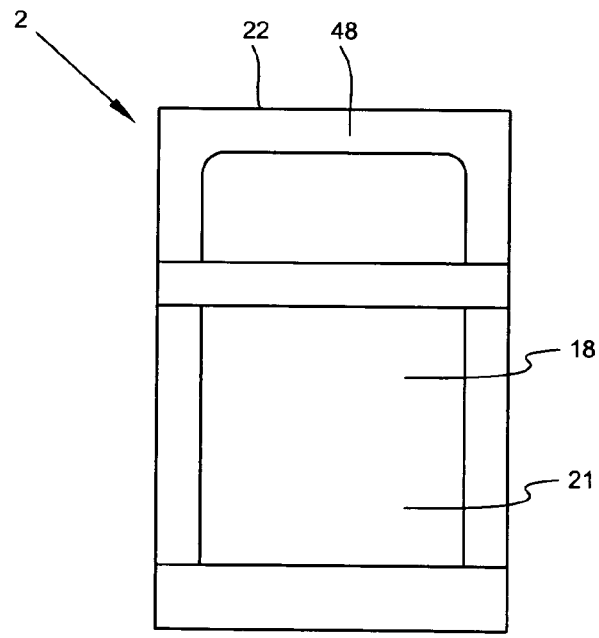
Fig. 6
Fig. 7

ADHESIVELY-SECURABLE MIRROR WIPE ASSEMBLY

RELATED APPLICATIONS

This application is a continuation-in-part of U.S. application Ser. No. 10/213,820, Aug. 8, 2002, now abandoned.

FIELD OF THE INVENTION

This invention relates to the field of devices to prevent mirrors from fogging over when exposed to a warmer more humid environment, and particularly to those mirrors used by dentists and other health care professionals to look inside of a patient's mouth.

BACKGROUND OF THE INVENTION

It is widely known that dentists use a small round mirror mounted at an angle at the end of an elongated shaft or handle, inserted into a patient's mouth to look behind the patient's teeth for problem areas. Such mirror surfaces fog up rapidly when entered into the patient's mouth, so the dentist has to withdraw the mirror and wipe off the condensation and coat the mirror surface with a material that tends to prevent fogging up.

Such prior art methods are time consuming, and the fogging-up deterring effect does not last very long. The prior art methods also require disposal of wiping cloths after each wipe or risk the danger of infection.

SUMMARY OF THE INVENTION

The mirror wipe assembly in accordance with the present invention avoids the problems of prior art methods and provides significant advantages over the prior art. It provides individually sealed mirror wipes in an impervious pouch protected from contamination by external sources such as air and other gaseous materials as well as from liquid materials. Each pouch has a single impervious pocket and a single mirror wipe strip of absorbent material on a backing strip, saturated with a substance that substantially prevents a mirror surface on which it is applied from fogging over. That substance comprises a surfactant material suspended in mineral oil, with a preservative also included such as benzalkonium chloride plus a disinfectant. A single mirror wipe strip can be used to wipe the mirror surface to keep it from fogging over while the mirror is being used on a single patient. That mirror wipe strip is then discarded, and a new pouch with a new mirror wipe strip saturated with the defogging substance is then used for the next patient that substantially reduces the risk of cross contamination and infection. The pouch in accordance with this invention comprises two sheets of flexible metalized material bonded together around their respective peripheral edges, defining a sealed impervious pocket in which the strip of absorbent material saturated with the defogging material is received. The very outer edges of a portion of the pouch are left unsealed whereby they can be gripped to pull them apart enough to open an entrance to the impervious pocket to withdraw the saturated absorbent strip for use. The metalized flexible sheet material of the pouch may be easily cut with a scissors or other cutting tool for access to the pocket in that way. An adhesive strip with a peel-off cover strip is provided on the back wall of the pouch for the user to adhere the pouch to any convenient surface while working on a patient. After wiping the absorbent strip across the surface of the mirror to defog it the first time, the absorbent strip may then be reinserted into the pocket of the pouch for convenient re-use when necessary while working on that particular patient. When finished with that particular patient, the absorbent strip and pouch used while working on that patient are then discarded.

BRIEF DESCRIPTION OF THE DRAWINGS

FIG. 4 is a side elevation view of the anti-fogging solution in a dispensing container for use in accordance with this invention.

FIG. 5 is a plan view of the absorbent strip in accordance with this invention to show its downwardly facing surface that is bonded to the upwardly facing surface of the backing strip.

FIG. 6 is a plan view of the backing strip in accordance with this invention to show its upwardly facing surface to which the downwardly facing surface of the absorbent strip is bonded.

FIG. 7 is a plan view of the metalized foil pouch in accordance with this invention showing one side thereof and one of the metalized foil sheets that forms the side shown.

DESCRIPTION OF PREFERRED EMBODIMENT

Figure 1:
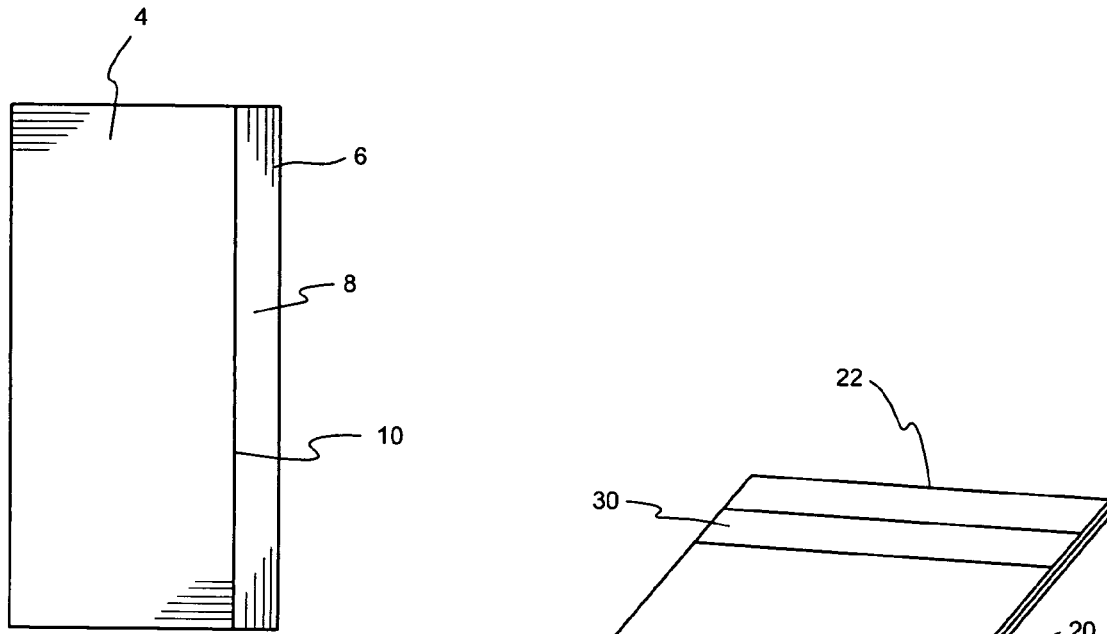
FIG. 1 is a plan view of an absorbent strip component of the mirror wipe assembly in accordance with this invention.
Figure 2:
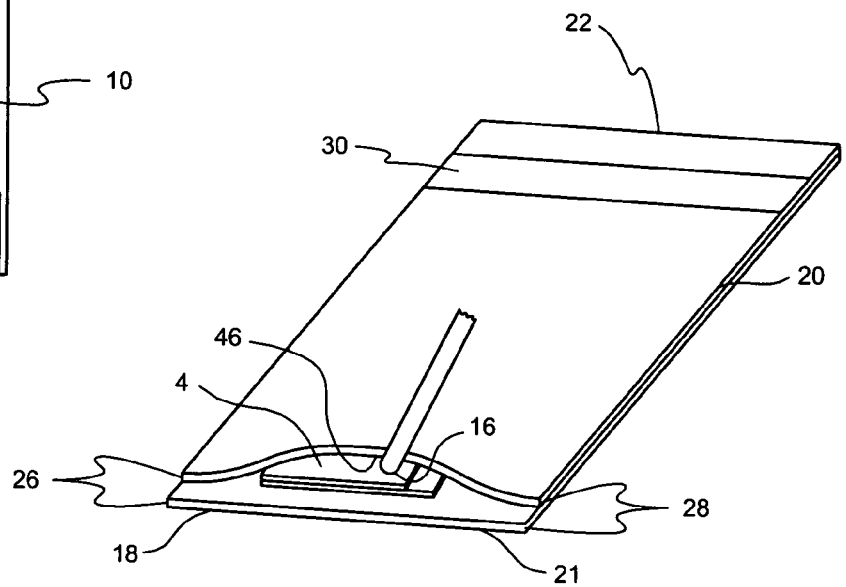
FIG. 2 is an end elevation view of the open end of a metalized foil pouch showing the absorbent strip received in the pocket thereof, and showing an anti-fogging solution being applied to saturate the absorbent strip before heat sealing the open end shut.
Figure 3:
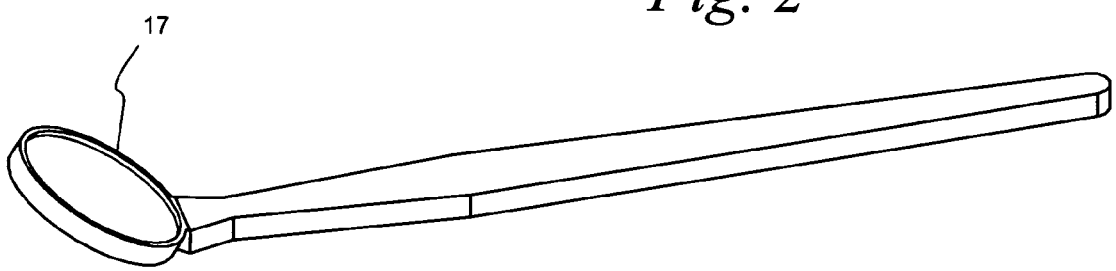
FIG. 3 is a perspective view of a dental mirror.
Figure 8:
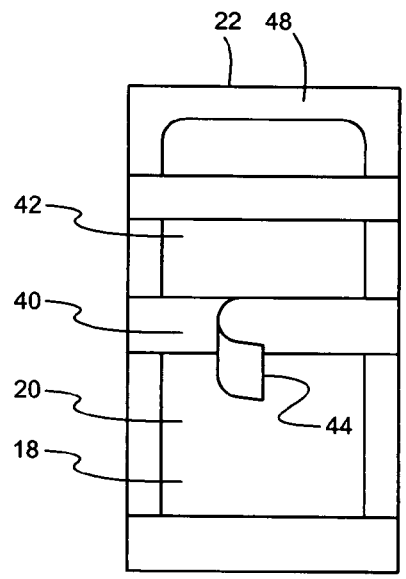
FIG. 8 is a plan view of the metalized foil pouch in accordance with this invention showing the other side thereof and the other one of the metalized foil sheets, this one having an adhesive strip on the outwardly facing surface to adhesively secure the pouch to a convenient location when in use, the adhesive strip being covered with a peel-off strip until ready for use.
Figure 9:
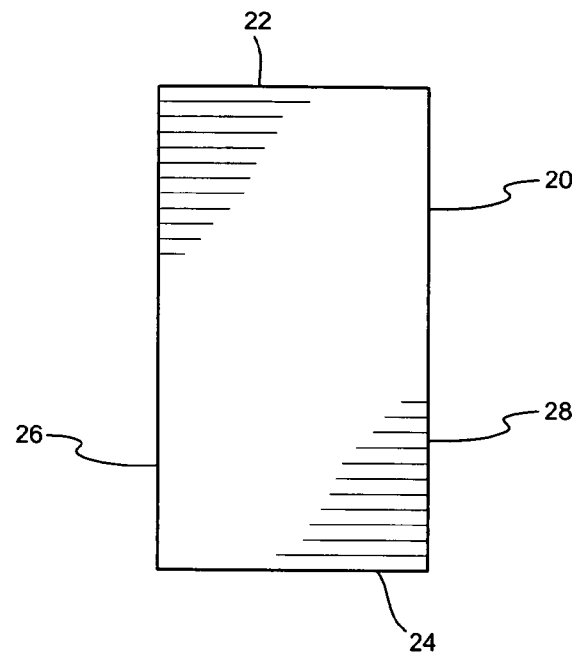
FIG. 9 is a plan view of one of the metalized foil sheets to form one side of the metalized foil pouch in accordance with this invention.
Figure 10:
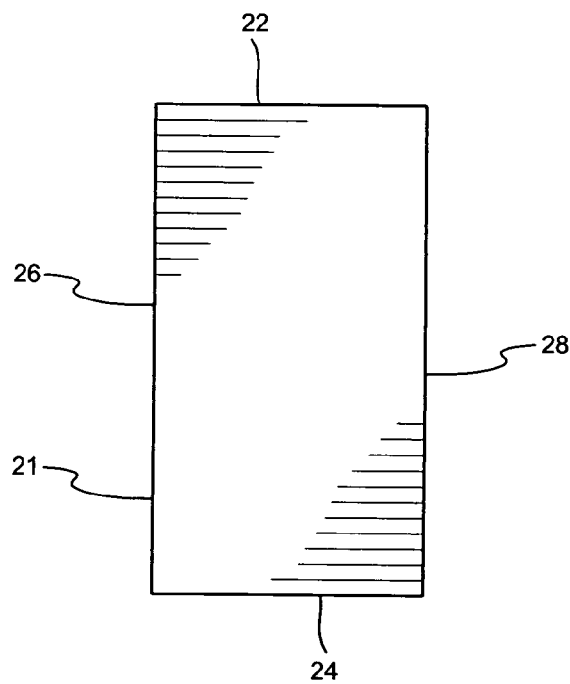
FIG. 10 is a plan view of the other one of the metalized foil sheets to form the other side of the metalized foil pouch in accordance with this invention.
Figure 11:
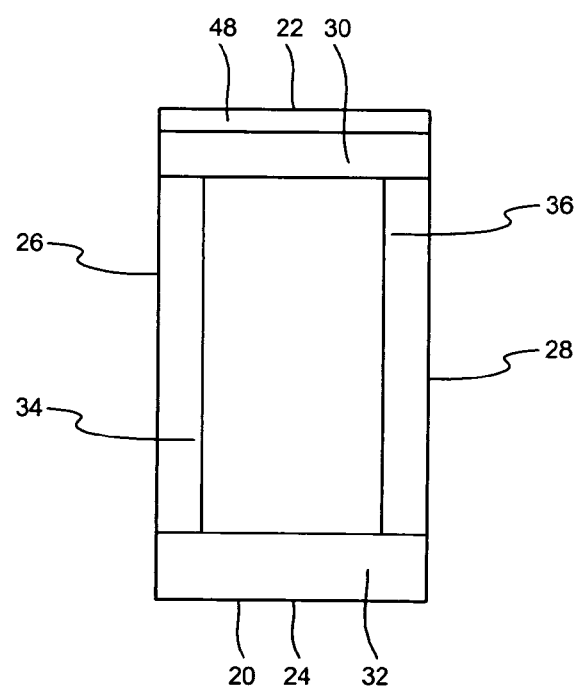
FIG. 11 is a plan view of the inwardly facing surface of one of the metalized foil sheets to form one side of the metalized foil pouch in accordance with this invention, showing the heat sealing strips along the edges of such inwardly facing surface.
Figure 12:
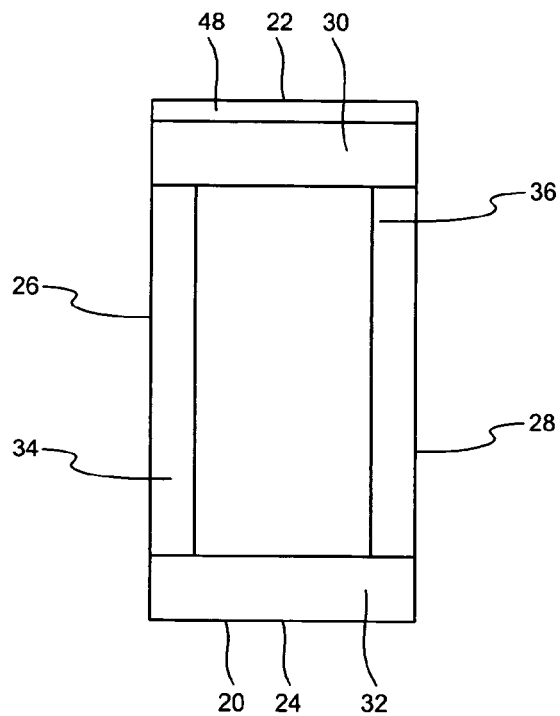
FIG. 12 is a plan view of the inwardly facing surface of the other one of the metalized foil sheets to form the other side of the metalized foil pouch in accordance with this invention, also showing the heat sealing strips along the edges of such inwardly facing surface.

The mirror wipe assembly 2 in accordance with the present invention comprises an absorbent strip 4 of foam material secured to a backing sheet 6 of polyethylene or comparable sheet material. The absorbent strip 4 is preferably about one inch wide and about three inches in length. It is made of an absorbent material such as open cell polyurethane. The backing sheet 6 is preferably about one and an eighth inches wide with a backing sheet border 8 about an eighth of an inch wide extending outwardly from one side edge 10 of the absorbent strip secured to the backing sheet 8. The backing sheet 6 is about three inches long, having an upwardly facing surface 12 to which the entire downwardly facing surface 14 of the absorbent strip 8 is secured. The backing sheet 8 is preferably a thin sheet of heat sealable plastic material such as polyethylene, and the absorbent strip 4 is bonded thereto by heat sealing.

A small amount of a liquid solution of transfer material 16 is applied to the absorbent strip 4, for transfer of a layer of such material to the mirror surface of a dental mirror 17 or other mirror surface when the mirror surface is wiped across the absorbent strip 4 for prevention of fogging-up when the mirror is placed in a dental patient's mouth. The transfer material 16 also includes a small amount of disinfectant material. A suitable transfer material having such properties and characteristics is available on the market known as Butler Clear Dip solution made by John O. Butler Co. of Chicago, Ill. and sold in dental supply stores. Any solution of transfer material 16 having such properties and characteristics is within the scope of this invention. The preferred embodiment of this invention is not limited to the specific transfer material identified as Butler Clear Dip solution. Other liquid solutions having a surfactant suspended in mineral oil with a preservative material such as benzylkonium chloride plus a small amount of disinfectant material may be used as the transfer material solution 16.

To protect the mirror wipe 2 and its absorbent strip 4 from exposure to the air, and to prevent loss or deterioration of the transfer material solution 16 applied to the absorbent strip 4 until ready for use, the mirror wipe 2 is enclosed within a metalized flexible foil pouch 18 which can be easily opened for withdrawing the mirror wipe 2 when ready for use. The pouch 18 comprises two sheets of flexible metalized foil, comprising a first metalized foil sheet 20 and a second metalized foil sheet 21. Each foil sheet includes a first relatively short end 22 having a dimension of about two inches and an opposite second relatively short end 24 having a dimension of about two inches, a first elongated side edge 26 about four inches long and an opposite second elongated side edge 28 about four inches long. At least one of the foil sheets 20 and 21, include a first short heat sealing strip 30 along the first end 22 extending inwardly thereof a short distance of about a half inch, a second short heat sealing strip 32 along the opposite second end 24 extending inwardly thereof a short distance of about a half inch, a third elongated heat sealing strip 34 along the first elongated side edge 26 extending inwardly therefrom a short distance of about a half inch, and a fourth elongated heat sealing strip 36 long the opposite second side edge 28 extending inwardly therefrom a short distance of about a half inch.

The metalized foil sheets 20 and 21 with heat sealing strips suitable for use in accordance with this invention are available from Technipaq, Inc., 975 Lutter Drive, Crystal Lake, Ill. However, it is within the scope of this invention to use other metalized foil strips and other means of bonding the outer edges of a superimposed pair of such sheets together to make the metalized pouch 18 in accordance with this invention. The preferred embodiment of this invention is not limited to use of the metalized foil sheets available from Technipaq, Inc. The metalized foil sheet 20 may comprise forty-eight gage metalized polyester and two mil of polyethylene, and the opposite metalized foil sheet 21 superimposed over sheet 20 may comprise forty-eight gage metalized polyester and two mil of peelable polyethylene.

The mirror wipe 2 and metalized pouch 18 in accordance with this invention are assembled as follows. The metalized sheet 20 is placed over the metalized sheet 21 with their respective side edges 26 in facing relationship and their respective side edges 28 in facing relationship, then heat sealed by applying a heat sealing bar thereto to close the side edges 26 and 28. The absorbent strip 4 secured to the backing strip 6 is laid on the metalized sheet 21 with the metalized sheet 20 over the top thereof. The end 22 has not been heat sealed at this time, but is still open. The liquid solution of transfer material 16 is then applied through the open end 22 to saturate the absorbent strip 4 inside of the pouch 18 between the side edges 26 and 28 with the transfer solution material 16. The open end 22 of the pouch 18 is then closed by heat sealing the ends 22 of the metalized foil sheets 20 and 21 together.

An adhesive material strip 40 is provided on the outwardly facing surface 42 of the metalized foil sheet 20, extending laterally across from side edge 26 to 28, and a peel-off cover strip 44 covers the adhesive strip 40 until ready to adhere the pouch 18 to a convenient surface for the user to withdraw the mirror wipe 2 from the pouch to wipe and defog the surface of a mirror, after which the mirror wipe 2 can be placed back into the pouch 18.

The metalized foil pouch 18 in accordance with this invention provides a sealed recess or pocket 46 that when closed seals the pocket 46 from outside air, fumes and other contaminants to protect the mirror wipe 2 therein from contamination and from deterioration of the transfer solution 16 by exposure to the ambient environment and air. The metalized foil sheets 20 and 21 are impervious to air, water and other materials, to prevent any such materials from the outside entering into the sealed pocket 46 and to prevent the transfer solution 16 from leaking out of the sealed pocket 46.

To access the pocket 46 for withdrawing the absorbent strip 4 with the transfer material 16 thereon, the outer edges 48 of the end 22 of the metalized foil sheets 20 and 21 are not completely bonded together so they can be grasped to pull apart. Also the metalized foil sheets 20 and 21 can be cut by a pair of scissors or other cutting instrument to provide an entrance to the pocket 46.

Figure 13:
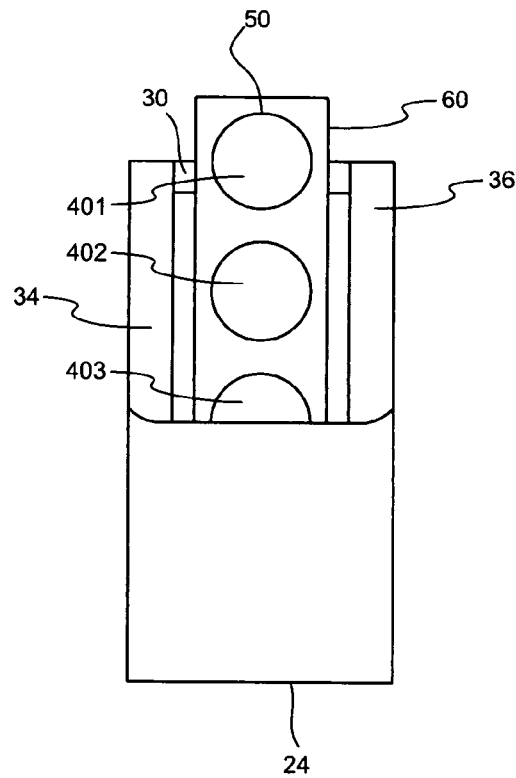
FIG. 13 is a plan view of the pouch in accordance with this invention having one of its sheets partially cut away to illustrate the elongated backing strip in the pocket of the pouch having a plurality of absorbent pads releasably adhered thereto.
Figure 14:
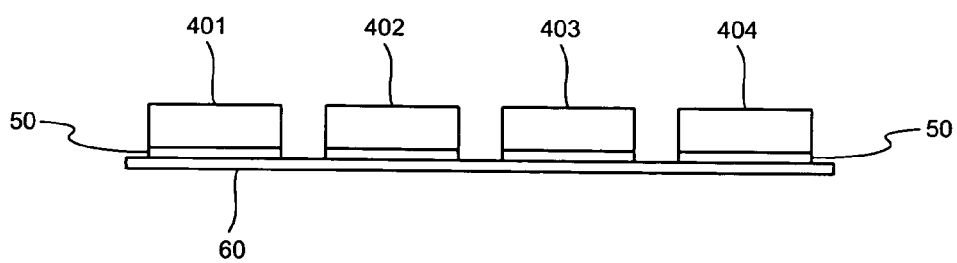
FIG. 14 is a side elevation view of the elongated backing strip seen in FIG. 13 and four absorbent pads adhered thereto.

A second embodiment of the invention is shown in FIGS. 13 and 14. In this embodiment the backing strip 60 is an elongated polyethylene strip, and the absorbent wiping components comprise a plurality of circular absorbent pads 401, 402, 403 and 404 releasably secured to the backing strip in spaced apart relationship by a special adhesive material 50 which the inventors discovered is able to maintain its adhesive characteristics even when the backing strip and absorbent pads thereon have been fully inserted into the pocket of the pouch and immersed in the anti-fogging transfer material 16.

The special adhesive material 50 is manufactured by 3M Company located at St. Paul, Minn., and marketed as SCOTCHMATE SJ3571. All of the other adhesive materials tried by the inventors lost their adhesive characteristic when the backing strip and absorbent pads thereon were immersed in the anti-fogging transfer material solution 16. The other adhesive materials tried turned to mush when immersed in such solution and could not hold the absorbent pads in place on the elongated backing strip 60.

When this embodiment of the invention is used, one end of the pouch is opened to gain access to the upper end of the elongated backing strip 60. The backing strip is then pulled upwardly and outwardly from the pouch to expose the uppermost absorbent pad 401. The dentist then pulls the pad 401 away from the elongated backing strip for use in wiping across the dental mirror to prevent or deter it from fogging over. The elongated backing strip 60 is then pushed back into the pocket of the pouch having the remaining absorbent pads 402, 403 and 404 thereon immersing them again in the anti-fogging solution until withdrawn for use when the mirror requires another application of the anti-fogging material.

I claim:

1. A anti-fogging mirror wipe assembly for a dentist comprising:
    a pouch having an impervious pocket bounded by an impervious peripheral wall to prevent entrance of water and other liquid materials as well as air and other gaseous materials from entering in said pocket when sealed, and to prevent such materials from escaping outwardly from said pocket when sealed;
    a backing strip inserted in said pouch;
    a material transfer member releasably adhered to said backing strip, said material transfer member having a material transfer substance thereon received in said pocket when sealed, said impervious peripheral wall of said pocket having an access portion for entrance to said pocket, said material transfer member being thereupon releasable from said pocket;
    an adhesive disposed upon said material transfer member to releasably adhere said material transfer member to said backing strip, said adhesive promoting the securing of said material transfer member to a convenient surface for a dentist to wipe a hand held mirror upon said material transfer member; and
    an anti-fogging material disposed in said material transfer member, whereby when said material transfer member is ultimately removed from said backing strip, then secured to a convenient surface by a dentist to allow the dentist to wipe a hand held mirror upon said material transfer member while positioned adjacent to a patient, said anti-fogging material promoting the examination of a patient's teeth without the hand held mirror fogging up, said adhesive promoting the securing of said material transfer member to said backing strip and, then to a convenient surface irrespective of the presence of said anti-fogging material in said pouch.

2. A mirror wipe assembly as set forth in claim 1, wherein said material transfer substance is a substance that is transferable to the surface of a mirror to prevent fogging of the mirror surface.

3. A mirror wipe assembly as set forth in claim 2, wherein said material transfer member includes an absorbent material to absorb said substance that is transferable to the surface of a mirror, and a backing strip, said absorbent material being held on said backing strip.

4. A mirror wipe assembly as set forth in claim 2, wherein said material transfer substance includes a surfactant material.

5. A mirror wipe assembly as set forth in claim 2, wherein said material transfer substance includes mineral oil.

6. A mirror wipe assembly as set forth in claim 2, wherein said material transfer substance includes benzylkonium chloride.

7. A mirror wipe assembly as set forth in claim 2, wherein said material transfer substance includes a small amount of a disinfectant material.

8. A mirror wipe assembly as set forth in claim 1, wherein said pouch comprises a peripheral wall of metalized foil material.

9. A mirror wipe assembly as set forth in claim 8, wherein said metalized foil material may be cut with a scissors to thereby gain entrance to said impervious pocket.

10. A mirror wipe assembly as set forth in claim 1, wherein said pouch comprises a first sheet of metalized foil material and a second sheet of metalized foil material superimposed on said first sheet of metalized foil material, said first and second sheets each having a peripheral edge extending entirely around, each of said peripheral edges of said first and second sheets being sealed together throughout the portions thereof adjacent said impervious pocket, said impervious pocket being bounded by said sealed together peripheral edges.

11. A mirror wipe assembly as set forth in claim 10, wherein at least one of said metalized foil sheets includes metalized polyester and polyethylene.

12. A mirror wipe assembly as set forth in claim 10, wherein at least one of said metalized foil sheets includes forty-eight gage metalized polyester and two mils of peelable polyethylene.

13. A mirror wipe assembly as set forth in claim 10, wherein a portion of said peripheral edges of said first and second sheets of metalized foil material outward from and remote from said impervious pocket are not sealed together to provide access for pulling adjacent portions of said sheets apart for access to said impervious pocket.

14. A method for preventing the fogging of a hand held mirror when inserted into a person's mouth, said method comprising the steps of:
    providing a pouch having an impervious pocket bounded by impervious peripheral walls to prevent entrance of water and other liquid materials as well as air and other gaseous materials from entering into said pocket when sealed, and to prevent such materials from escaping outwardly from said pocket when sealed, said impervious peripheral walls of said pocket having an access portion for entrance to said pocket, wherein said impervious walls bounding said pocket include an inwardly facing surface facing inwardly of said pocket and an outwardly facing surface facing outwardly of said pocket;
    inserting a backing strip in said pocket;
    providing an adhesive that detachably secures at least one absorbent member to said backing strip, said adhesive ultimately promoting the detachable securing of said absorbent member to a selected location that promotes the wiping of a hand held mirror upon said absorbent member; and
    disposing an anti-fogging material in said pocket for absorption by said absorbent member, whereby a dentist wipes a hand held mirror upon said absorbent member after being secured to a selected location, the hand held mirror ultimately being inserted into a patient's mouth without fogging up thereby allowing the dentist to look behind the patient's teeth, whereupon, the absorbent member is removed from the selected location and discarded, and the backing strip with any remaining absorbent members detachably secured thereto, is pushed back into said pouch.

15. A mirror wipe assembly for dentists comprising:
    a pouch having a pocket therein, said pouch being openable at one end for access to said pocket;
    a backing strip loosely received in said pocket for withdrawal therefrom and for reinsertion therein;

an absorbent member releasably adhered to said backing strip;

a special adhesive on said absorbent member to releasably adhere said absorbent member to said backing strip, said special adhesive promoting the securing of said absorbent member to a selected location after said absorbent member is removed from said backing strip; and an anti-fogging material in said pocket for absorption by said absorbent member, said special adhesive retaining its adherent characteristic even though exposed to said anti-fogging material in said pocket of said pouch, whereby a dentist is capable of wiping a hand held mirror upon said absorbent member when secured to the selected location, inserting the hand held mirror into a patient's mouth without the mirror fogging up, then removing the absorbent member from the selected location after looking behind the patient's teeth, whereupon, the absorbent member may be discarded and the backing strip, with any remaining absorbent members secured thereto, may be pushed back into said pouch.

16. A mirror wipe assembly as set forth in claim 15, wherein said backing strip comprises an elongated strip of polyethylene and said absorbent member comprises a pad of absorbent material.

17. A mirror wipe assembly as set forth in claim 16 wherein said pad of absorbent material is circular, wherein said mirror wipe assembly includes a plurality of pads of absorbent material including said pad of absorbent material that is circular, said plurality of pads of absorbent material being releasably adhered to said elongated backing strip in spaced apart relationship thereon.

18. A mirror wipe assembly as set forth in claim 15, wherein said pocket includes disinfectant material.

* * * * *